United States Patent
Qian

(10) Patent No.: US 10,118,966 B2
(45) Date of Patent: Nov. 6, 2018

(54) ANTI-EGFR MONOCLONAL ANTIBODY, METHODS OF MAKING, AND USES THEREOF IN THE TREATMENT OF CANCER

(71) Applicant: Shanghai Biomabs Pharmaceuticals Co., Ltd., Shanghai (CN)

(72) Inventor: Weizhu Qian, Shanghai (CN)

(73) Assignee: Shanghai Biomabs Pharmaceuticals Co., Ltd., Shanghai (CN)

( * ) Notice: Subject to any disclaimer, the term of this patent is extended or adjusted under 35 U.S.C. 154(b) by 0 days.

(21) Appl. No.: 15/541,291

(22) PCT Filed: Jan. 4, 2016

(86) PCT No.: PCT/CN2016/070024
§ 371 (c)(1),
(2) Date: Jun. 30, 2017

(87) PCT Pub. No.: WO2016/110226
PCT Pub. Date: Jul. 14, 2016

(65) Prior Publication Data
US 2018/0030139 A1  Feb. 1, 2018

(30) Foreign Application Priority Data
Jan. 7, 2015 (CN) .......................... 2015 1 0006233

(51) Int. Cl.
| | | |
|---|---|---|
| *C07K 16/28* | (2006.01) | |
| *C07K 16/30* | (2006.01) | |
| *A61K 39/395* | (2006.01) | |
| *A61K 31/4745* | (2006.01) | |
| *A61K 31/513* | (2006.01) | |
| *A61K 45/06* | (2006.01) | |
| *A61K 31/519* | (2006.01) | |
| *A61K 39/00* | (2006.01) | |

(52) U.S. Cl.
CPC ...... *C07K 16/2863* (2013.01); *A61K 31/4745* (2013.01); *A61K 31/513* (2013.01); *A61K 31/519* (2013.01); *A61K 39/39558* (2013.01); *A61K 45/06* (2013.01); *C07K 16/30* (2013.01); *C07K 16/3046* (2013.01); *A61K 2039/505* (2013.01); *A61K 2039/545* (2013.01); *C07K 2317/14* (2013.01); *C07K 2317/51* (2013.01); *C07K 2317/515* (2013.01)

(58) Field of Classification Search
CPC ............... C07K 16/2863; C07K 16/30; C07K 16/3046; C07K 2317/14; C07K 2317/51; C07K 2317/515; A61K 31/519; A61K 39/39558; A61K 45/06; A61K 31/4745; A61K 31/51; A61K 2039/505; A61K 2039/545
See application file for complete search history.

(56) References Cited

U.S. PATENT DOCUMENTS

| | | | | |
|---|---|---|---|---|
| 8,992,932 | B2 * | 3/2015 | Lerchen ................. | C07K 16/30 424/179.1 |
| 2011/0045496 | A1 * | 2/2011 | Bosques ............ | G01N 33/5308 435/7.21 |

FOREIGN PATENT DOCUMENTS

WO    2004/085474 A2    10/2004

OTHER PUBLICATIONS

Wang C, et al. (Jan./Feb. 2011). mAbs. 3(1):67-75. https://doi.org/10.4161/mabs.3.1.14021.*
Chamberlain P. (Jun. 25, 2014). 2014(4):23-43. https://doi.org/10.2147/BS.S50012.*
Duang, X. et al. "Research Advances of Animal Cell Culture Medium for Producing Antibody Drugs" Chinese Medicinal Biotechnology, vol. 9, No. 1 Feb. 28, 2014, 5 pages.
Song, S. et al. "Advancies in Medical Treatment of Metastatic Colorectal Cancer" China Oncology, vol. 16, No. 10, Oct. 28, 2006, 6 pages.
International Search Report issued in corresponding PCT Application No. PCT/CN2016/070024, dated Apr. 11, 2016, 3 pages.
NIH National Cancer Institute, Cetuximab, www.cancer.gov/about-cancer/treatment/drugs/cetuximab, published online Oct. 23, 2014, updated Mar. 9, 2018, 2 pages.
Australian Government—IP Australia, Examination Report No. 1, Application No. 2016206155, dated Mar. 8, 2018, 5 pages.

* cited by examiner

*Primary Examiner* — Robert S Landsman
(74) *Attorney, Agent, or Firm* — Quarles & Brady LLP

(57) ABSTRACT

The present invention provides a method for producing an anti-EGFR monoclonal antibody and the applications thereof. The method comprises the steps of: designing and synthesizing the light chain and heavy chain according to the codons preferred by Chinese hamster, transfecting GS knockout host cells CHO-CR-GS-/-, culturing cells using serum-free technology, isolating and purifying the antibody, and obtaining the low immunogenicity CMAB009 antibody.

42 Claims, 7 Drawing Sheets
Specification includes a Sequence Listing.

ANTI-EGFR MONOCLONAL ANTIBODY, METHODS OF MAKING, AND USES THEREOF IN THE TREATMENT OF CANCER

CROSS-REFERENCE TO RELATED APPLICATIONS

This application represents the national stage entry of PCT International Application PCT/CN2016/070024 filed Jan. 4, 2016 and claims priority to pending Chinese Patent Application 201510006233.7 filed Jan. 7, 2015. The contents of this application are hereby incorporated by reference as if set forth in their entirety herein.

FIELD OF THE INVENTION

The present invention relates to biotechnology, particularly the producing method and applications of a novel anti-EGFR monoclonal antibody.

BACKGROUND OF THE INVENTION

Tumor, particularly malignant tumor, is a disease which cause serious harm to human health in today's world, and is the $2^{nd}$ deadly among all diseases. But in recent years, the incidence rate was significantly increased. The malignant cancer has poor treatment, accompanied with high metastasis rate at late stage and poor prognosis. Current conventional clinical treatment methods including radiotherapy, chemotherapy and surgery, which although largely alleviate the pain and prolong the survival time, have significant limitations, and are difficult to improve their efficacy further.

Proliferation of normal cells is strictly controlled by respective ligands activating their growth factor receptors, such as growth factor receptor tyrosine kinases. Cancer cell proliferation is also through its factor receptor activation, but it loses the strict control of normal proliferation. This loss of control may be caused by many reasons, such as growth factor over-expression, overexpression of growth factor receptors, or spontaneous activation of biochemical pathways regulated by growth factors. Oncogenic receptors include epidermal growth factor receptor (EGFR), platelet derived growth factor receptor (PDGFR), insulin-like growth factor receptor ((IGFR), nerve growth factor receptor (NGFR), and fibroblast growth factor receptor ((FGF) etc.

Epidermal growth factor receptor (EGFR) is also known as c-erbB1/HER1, whose family members are growth factor receptor tyrosine kinases, their cell surface with specific growth factors or natural ligand interactions, such as with EGF or TGF ci interactions, thereby activating the receptor tyrosine kinases. The first member of the family has been found to be a glycoprotein with apparent molecular weight of 165 KD.

EGFR plays an important role in the regulation of tumor cell growth, repair and survival, angiogenesis, invasion and metastasis, and is expressed in a considerable number of human tumors. In many malignant tumors, the expression of EGFR is often associated with a poor prognosis and a low survival rate. Based on this, if there is a drug which can block EGFR activity, it will inhibit the phosphorylation and signal transduction, thus play an anti-tumor functions in multiple aspects, and increase the anti-tumor chemotherapy and radiotherapy treatment. In some studies, EGFR inhibitors show addictive and synergistic effects when used in combined treatment with various chemotherapy drugs and radiation therapy drugs for certain cancers.

EGFR inhibitors include monoclonal antibodies, tyrosine kinase inhibitors, quinazoline pyrrolo-/pyrrolo-/pyridopyridines, ligand-toxin and immunotoxin complexes, as well as antisense oligonucleotides and EGFR/ligand mediated vaccines.

It was demonstrated in some in vivo and in vitro experiments that the anti-EGFR antibody can successfully inhibit the growth of EGFR-expressing tumor cell lines. In treatment of solid tumors, the results from some anti-EGFR monoclonal antibodies alone or their combination with traditional treatment methods are encouraging.

Glycosylation is a protein important post-translational modifications. Protein molecular surface sugar chains can have a profound impact on the structure and function of the protein molecules, glycosylation as an important post-translation process, has a great impact on proper proteins folding, localization, immunogenicity and biological activity. The glycosylation and glycan structure of mAb antibody have strong correlation with its function, by affecting the binding of IgG molecules to FcRs, Clq and FeRn to regulate the antibody-dependent cellular cytotoxicity (ADCC), complement-dependent cytotoxicity (CDC) and half-life of IgG molecules. Glycosylation also affects the safety features of mAb, particularly non-human glycans, and has potential immunogenicity. The glycans located in Fab functional region can affect both the safety and efficacy features of these drugs.

Glycosylation is highly dependent on cell expression system and subclone selection, and many factors during cell culture, for example medium components, culture conditions will affect glycosylation, thereby affecting the biological activity, efficacy, immunogenicity and pharmacokinetics of therapeutic proteins.

Among the therapeutic monoclonal antibodies currently marketed, the vast majority is produced by recombinant DNA technology, and the vast majority use in vitro cell culture technology. Because of the complexity of mammalian cell structure, function and gene expression regulation, there is a big difference between the expression of exogenous genes in mammalian cells and that in prokaryotes, consequently, the machinery for efficient expression of exogenous genes is also different from that for prokaryotes cells. Expression of exogenous gene in mammalian cells includes gene transcription, mRNA translation and post-translational modifications etc. Post-translational modifications include glycosylation, phosphorylation, oligomerization, as well as the formation of intra- or intermolecular disulfide bonds between protein molecules. Post-translational modification is crucial to the function of the protein, so it may be necessary to express certain proteins with biological functions in mammalian cells, such as membrane proteins, antibodies and enzymes having specific catalytic function. CHO cells and mouse myeloma cells (NS0, SP2/0) expression system has currently become the golden standard as cell engineering system for therapeutic antibody and Fc-fusion proteins. According to statistics, 48% of currently approved therapeutic monoclonal antibodies are expressed in CHO cells, while 45% are expressed in murine cells (21% NS0 cells, 14% SP2/0 cells, 10% hybridoma cells). Although the integrity of polypeptide chains in different expression systems and culture conditions seems unchanged, the changes of glycosylation types cannot be ignored.

Cetuximab (Erbitux®, C225 mab), is a recombinant chimeric monoclonal antibody specifically targeting epidermal growth factor receptor (EGFR), and was approved in many countries for the treatment of metastatic colorectal cancer and head and neck squamous cell carcinoma. However, a number of studies have reported that the drug hypersensitivity reactions occur at very high incidence in clinical applications. Drug specific IgE antibodies were found in the serum of most patients with hypersensitivity reactions, and it specifically reacts against α-Gal. Further research found that, Erbitux® is expressed and prepared in mammalian cells (mouse myeloma cells SP2/0), and this murine cell line containing an additional α1,3-galactosidase transferase, which primarily mediates the transfer of galactose residue is from UDP-Gal of a conformation to the terminal galactose residues, thereby generating α-Gal. α-Gal is a harmful non-human disaccharide, found in certain glycans on mAb, especially mAb expressed in the murine cell lines. High levels of anti-α-Gal IgE antibodies were found in some patients. If using mAb with glycan containing α-Gal units for treatment, there will be serious hypersensitivity reactions. Further, the difference of murine cell IgG glycosylation from human is that, murine cells not only have the biosynthetic machinery to produce α-Gal epitope, but also produce N-hydroxyethyl neuraminidase (NGNA), rather than N-acetyl phenol neuraminidase (NANA). The distinction of NGNA and NANA is there is an additional oxygen atom in NGNA, and glycoproteins are considered to be closely associated with the immunogenicity in humans if they contain NGNA residues. Some marketed therapeutic glycoproteins have cause serious adverse reactions in the patients because they contains NGNA residues.

SUMMARY OF THE INVENTION

In order to overcome the disadvantage of using SP2/0 cells as the host cell to produce anti-EGFR monoclonal antibody, it's necessary to use a suitable host cell and optimize the culture conditions to reduce the differences between proteins expressed in cell culture and natural human proteins, so as to improve the drug safety for human.

The present inventors use CHO cells as host cells, culture cells in serum-free condition, successfully produce genetically engineered anti-EGFR antibody (CMAB009 mAb) with different glycan structures. Because this antibody does not contain the α-Gal glycan structure, it would not cause drug-specific IgE antibody-mediated hypersensitivity; there are no endogenous retrovirus particles in the engineered cells, there is no contamination in the antibody obtained from the cell culture of the engineered cells. The anti-EGFR monoclonal antibody prepared by this method has better clinical safety than Erbitux® mAb.

A novel method of producing an anti-EGFR monoclonal antibody, said method comprising:
a) a novel anti-EGFR monoclonal antibody comprises a light chain comprising the amino acid sequence of SEQ ID NO:2 and a heavy chain comprising the amino acid sequence of SEQ ID NO: 4;
b) constructing recombinant plasmid using nucleic acid fragment of SEQ ID NO:1 and SEQ ID NO:3, transfecting host cell, screening high-expressing clone;
c) optimizing cell culture conditions, culturing in large scale to produce novel anti-EGFR monoclonal antibody, isolating and purifying.

The coding sequences for the light chain and heavy chain of the novel anti-EGFR monoclonal antibody are designed and synthesized according to the codons mostly preferred by Chinese hamster.

The host cell is Eukaryotic mammalian CHO cell.

The cell culture temperature is 33° C.~36° C., preferably 34° C.

The pH of the cell culture growth media is 6.5~6.9, preferably pH6.6.

The osmotic pressure of the cell culture growth media is 290 mOsm/kg~350 mOsm/kg, preferably 340 mOsm/kg.

The culture media is serum-free culture media, and the host cell is cultured in serum-free condition.

A composition comprising the antibody of CMAB009, and a pharmaceutically acceptable carrier.

A method of producing drug comprising the novel anti-EGFR monoclonal antibody of CMAB009 to treat tumors expressing epidermal growth factor receptor (EGFR).

A method of treating tumors expressing epidermal growth factor receptor (EGFR) with drug comprising the composition of CMAB009 and a pharmaceutically acceptable carrier.

A method of further comprising administering in combination with other drugs treating tumors expressing epidermal growth factor receptor (EGFR).

A liquid pharmaceutical composition comprising water and an anti-EGFR antibody,
wherein the anti-EGFR antibody comprises a light chain comprising the amino acid sequence set forth in SEQ ID NO: 2 and a heavy chain comprising the amino acid sequence set forth in SEQ ID NO: 4, wherein the antibody has a z-average (z-avg) of about 10-25 nm as determined by dynamic light scattering (DLS) analysis, and wherein the anti-EGFR antibody does not comprise an N-glycolyl-neuraminic acid (NGNA), does not comprise a Gal-α(1,3)-Gal glycan, and/or does comprise a Gal-α(2, 3/6)-Gal glycan.

The composition comprising water and an anti-EGFR antibody, wherein the z-avg of the antibody is 15-20 nm.

A method of treating a human subject having cancer, said method comprising administering the composition to the subject, such the cancer is treated.

A method of inhibiting progression of cancer in a human subject, said method comprising administering the composition to the subject, such progression is inhibited.

The cancer is squamous cell carcinoma of the head and neck (SCCHN) or colorectal cancer.

The colorectal cancer is K-Ras Wild-type, EGFR-expressing colorectal cancer.

The antibody is administered in combination with FOLFIRI (irinotecan, 5-fluorouracil, leucovorin).

The antibody is administered in combination with irinotecan.

The subject has recurrent or metastatic squamous cell carcinoma of the head and neck and has failed prior platinum-based therapy.

The subject has locally or regionally advanced squamous cell carcinoma of the head and neck.

The antibody is administered in combination with radiation therapy for the initial treatment of the cancer.

The subject has recurrent locoregional disease or metastatic squamous cell carcinoma of the head and neck.

The antibody is administered in combination with platinum-based therapy with 5-FU.

The antibody is administered in combination with an additional therapeutic agent.

The additional therapeutic agent is a chemotherapeutic agent.

The subject has failed oxaliplatin and fluoopyrimidine-based chemotherapy.

A method of treating or inhibiting progression of colorectal cancer in a subject having colorectal cancer, said method comprising administering an anti-EGFR antibody and irinotecan, such that colorectal cancer is treated, wherein the antibody comprises a light chain comprising the amino acid sequence set forth in SEQ ID NO: 2, comprises a heavy chain comprising the amino acid sequence set forth in SEQ ID NO: 4, and contains a Gal-α(2, 3/6)-Gal glycan.

A method of treating or inhibiting progression of colorectal cancer in a subject having colorectal cancer, said method comprising administering an anti-EGFR antibody and irinotecan, such that colorectal cancer is treated, wherein the antibody comprises a light chain comprising the amino acid sequence set forth in SEQ ID NO: 2, comprises a heavy chain comprising the amino acid sequence set forth in SEQ ID NO: 4, and does not contain either an N-glycolylneuraminic acid (NGNA) glycan or a Gal-α(1,3)-Gal glycan.

The colorectal cancer is advanced colorectal cancer.

The antibody is administered via infusion to the subject at an initial dose of 400 mg/m$^2$ followed by a weekly dose of 250 mg/m$^2$.

The antibody is produced in a Chinese Hamster Ovary (CHO) cell.

A liquid pharmaceutical composition comprising water and an anti-EGFR antibody,
wherein the anti-EGFR antibody comprises a light chain comprising the amino acid sequence set forth in SEQ ID NO: 2 and a heavy chain comprising the amino acid sequence set forth in SEQ ID NO: 4, wherein the anti-EGFR antibody is produced in a Chinese Hamster Ovary (CHO) cell, and wherein the composition does not comprise a polysorbate and/or a saccharobiose.

A liquid pharmaceutical composition consisting essentially of water, an anti-EGFR antibody, sodium chloride, sodium dihydrogen phosphate dihydrate, and disodium phosphate dihydrate, wherein the anti-EGFR antibody comprises a light chain comprising the amino acid sequence set forth in SEQ ID NO: 2 and a heavy chain comprising the amino acid sequence set forth in SEQ ID NO: 4, and wherein the anti-EGFR antibody does not comprise an N-glycolylneuraminic acid (NGNA) glycan, does not comprise a Gal-α(1,3)-Gal glycan, and/or does comprise a Gal-α(2, 3/6)-Gal glycan.

DETAILED DESCRIPTION

Figure 1:
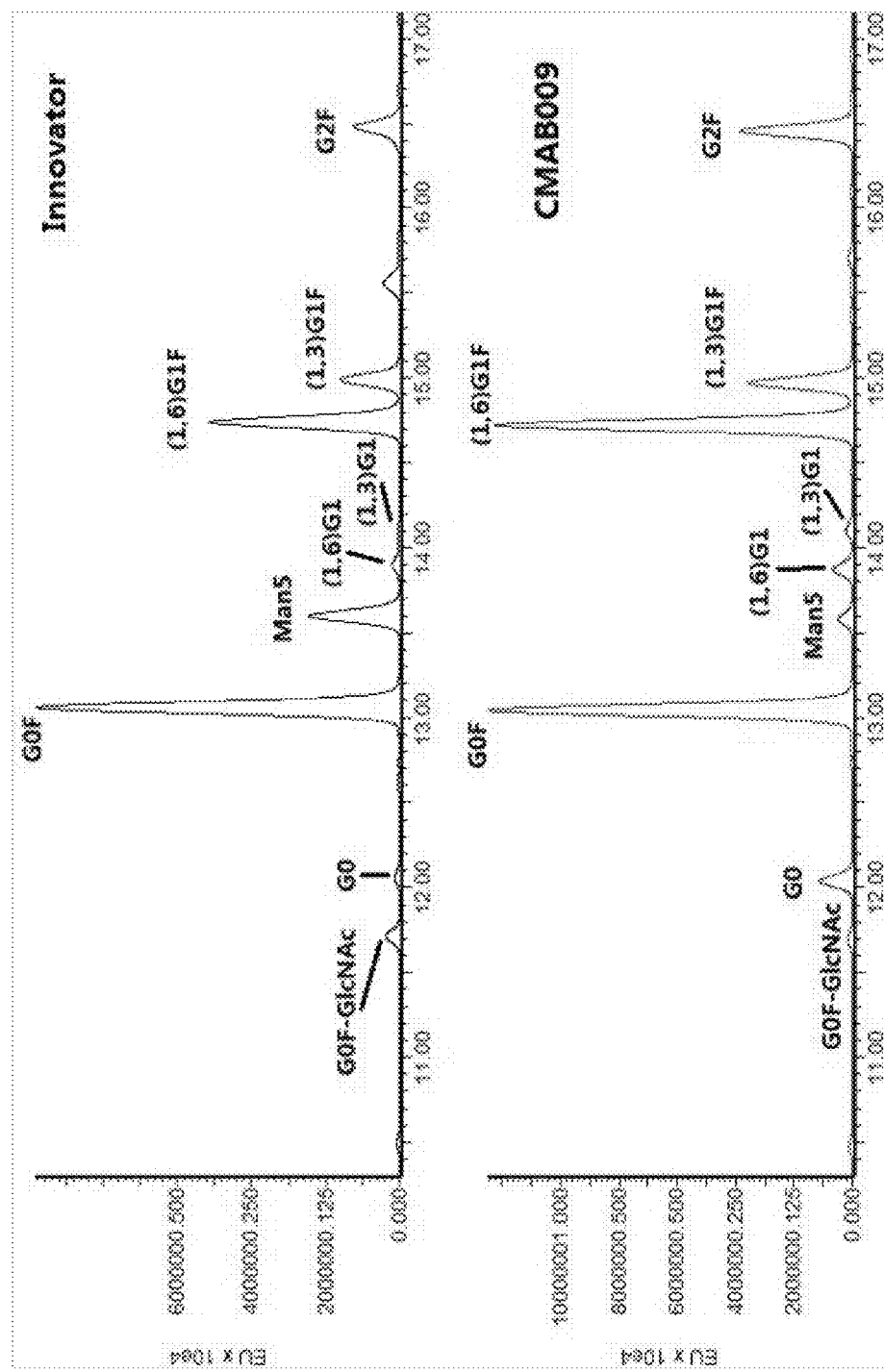
FIG. 1 LC/MS analysis of Cetuximab and CMAB009 heavy chain Fc segment oligosaccharides fluorescence labeling chromatogram FIG. 2 LC/MS analysis of Cetuximab and CMAB009 heavy chain Fab fragment oligosaccharides fluorescence labeling chromatogram FIG. 3 Fortebio Octet immunogenicity analysis (Octet QK System)

The invention is based, at least in part, on the therapeutic advantages of producing an anti-EGFR antibody in Chinese Hamster Ovary (CHO) cells. CMAB009 is an anti-EGFR antibody that is produced in CHO cells and has the amino acid sequences of cetuximab. In comparison to Erbitux® (cetuximab), administration of CMAB009 to patients having cancer showed reduced immunogenicity reactions and improved efficacy, including an increase in the time in which the disease progressed.

As used herein, the term "cetuximab" refers to an anti-EGFR antibody having a light chain comprising the amino acid sequence set forth in SEQ ID NO: 2, and a heavy chain comprising the amino acid sequence set forth in SEQ ID NO: 4. The sequences of the cetuximab light and heavy chains are described below:

```
Gatatccttctgacacagtctccagtgatactgtcagtttctccaggggagcgcgtctca        60

Tttagttgtcgggccagtcagagtatcggcacaaacatccattggtaccagcagcggaca        120

Aacggctccccccggttgctcattaagtacgcaagcgagtctatctctgggataccaagt        180

Cgcttctcgggtagtggtagcggaacagattttactctgagtatcaatagcgtcgaatcc        240

Gaagatattgccgattactactgtcagcagaataacaactggccaaccacattcggcgcc        300

Ggtaccaagctggaactcaagcgcacagttgccgcacctagtgtcttcatcttcccacca        360

Tctgacgagcaactaaagagtggcactgcaagtgtcgtatgtctgctgaacaactttac         420

Ccacgggaggctaaagtgcagtggaaggtagacaacgcccttcagagcggaaattctcag       480

Gaaagcgtcaccgaacaagattccaaggatagcacatactccctgtcctctaccctgaca       540

Ctgtcaaaagctgactacgaaaagcataaagtgtatgcttgcgaggtgactcatcagggg      600

Ctcagctcgcccgtcaccaagtccttcaaccgtggagaatgt (SEQ ID NO: 1)

DILLTQSPVILSVSPGERVSFSCRASQSIGTNIHWYQQRTNGSPRLLIKYASESISGIPS        60

RFSGSGSGTDFTLSINSVESEDIADYYCQQNNNWPTTFGAGTKLELKRTVAAPSVFIFPP       120
```

```
SDEQLKSGTASVVCLLNNFYPREAKVQWKVDNALQSGNSQESVTEQDSKDSTYSLSSTLT            180

LSKADYEKHKVYACEVTHQGLSSPVTKSFNRGEC (SEQ ID NO: 2)

DILLTQSPVILSVSPGERVSFSCRASQSIGTNIHWYQQRTNGSPRLLIKYASESISGIPS             60

RFSGSGSGTDFTLSINSVESEDIADYYCQQNNNWPTTFGAGTKLELKR (SEQ ID NO: 5;

variable region of light chain, the CDRs were marked yellow)

CDR1
                                                           (SEQ ID NO: 6)
                              RASQSIGTNIH

CDR2
                                                           (SEQ ID NO: 7)
                              YASESIS

CDR3
                                                           (SEQ ID NO: 8)
                              QQNNNWPTT
``` caggtgcagctgaagcagagcggaccaggcctggtccagccctcacagtccctgagcatt    60

Acttgtactgtgagtgggttctcgttgacgaactacggggtgcattgggtgcgccagagt    120

Cccggtaaagggctggagtggttaggcgtgatttggagcggcggtaacactgactataat    180

Accccttttaccagtcgcttgagtatcaataaggataattcaaagtctcaagtgtttttt    240

Aagatgaactccctacagagcaacgatacggctatctactactgtgcccgcgcccttaca    300

Tactacgactatgagttcgcttattggggccaggggaccttggtcactgtgtctgcagct    360

Tctacaaaagggccatccgtgttcccactggccccccagttccaagagcactagtggtggc    420

Acagcagccctcgggtgcctcgtgaaggattacttcccggagccagtgaccgtcagttgg    480

Aactccggcgctctaacaagcggagtacatacttttccagccgtgctgcagtcttcaggg    540

Ctttacagtcttcctccgttgtgacagtgcccagcagcagcctgggcacccagacttat    600

Atttgtaatgtgaaccataagccttctaatactaaggtggacaagagagttgagccaaag    660 tcctgtgacaaaactcacacatgcccccccttgcccagctcctgagttgttgggcggccct    720 tccgtcttcctgtttccccgaaacctaaggatacccctgatgatatctcggacaccagaa    780 gtgacatgcgtcgtggtcgatgtgtcacacgaagaccctgaggtgaaatttaactggtac    840 gtagacggtgtagaagttcacaacgctaagacaaagcctcgggaagagcagtacaactca    900 acctaccgagtagtgtccgtgcttactgttctgcaccaggactggctgaatggaaaggaa    960 tataagtgtaaagtgtccaataaggcactgcctgctccaatcgagaagacgatttctaaa    1020 gccaagggacaaccaagagaacctcaggtgtataccttgcccccatctgagaagagatg    1080 accaaaaaccaggtgtcacttacatgcctcgtgaaaggcttctatccttctgacattgcc    1140 gtcgaatgggagagtaacggacagcccgagaacaactacaagaccacacctccagtgctg    1200 gattcggatggctcttttcttcctttatagtaagctcactgtggacaagtcccgatggcag    1260 caggggaacgtgttctcttgcagcgtgatgcacgaggcattgcataatcactacacccag    1320 aagtctctctcattatcccctggcaag (SEQ ID NO: 3)

```
QVQLKQSGPGLVQPSQSLSITCTVSGFSLTNYGVHWVRQSPGKGLEWLGVIWSGGNTDYN             60

TPFTSRLSINKDNSKSQVFFKMNSLQSNDTAIYYCARALTYYDYEFAYWGQGTLVTVSAA            120

STKGPSVFPLAPSSKSTSGGTAALGCLVKDYFPEPVTVSWNSGALTSGVHTFPAVLQSSG            180

LYSLSSVVTVPSSSLGTQTYICNVNHKPSNTKVDKRVEPKSCDKTHTCPPCPAPELLGGP            240

SVFLFPPKPKDTLMISRTPEVTCVVVDVSHEDPEVKFNWYVDGVEVHNAKTKPREEQYNS            300

TYRVVSVLTVLHQDWLNGKEYKCKVSNKALPAPIEKTISKAKGQPREPQVYTLPPSREEM            360

TKNQVSLTCLVKGFYPSDIAVEWESNGQPENNYKTTPPVLDSDGSFFLYSKLTVDKSRWQ            420
```

-continued

QGNVFSCSVMHEALHNHYTQKSLSLSPGK (SEQ ID NO: 4)

QVQLKQSGPGLVQPSQSLSITCTVSGFSLTNYGVHWVRQSPGKGLEWLGVIWSGGNTDYN         60

TPFTSRLSINKDNSKSQVFFKMNSLQSNDTAIYYCARALTYYDYEFAYWGQGTLVTVSA (SEQ ID

NO: 9; variable region of light chain, the CDRs were marked yellow)

```
                    CDR1
                                                  (SEQ ID NO: 10)
                    NYGVH

CDR2
                                                  (SEQ ID NO: 11)
                    VIWSGGNTDYNTPFTS

CDR3
                                                  (SEQ ID NO: 12)
                    ALTYYDYEFAY
```

As used herein, the term "CMAB009" refers to a cetuximab antibody which is produced in a CHO cell. Thus, the CMAB009 antibody comprises a light chain comprising the amino acid sequence set forth in SEQ ID NO: 1 and a heavy chain comprising the amino acid sequence set forth in SEQ ID NO: 3. Further, the CMAB009 antibody does not contain either an N-glycolylneuraminic acid (NGNA) glycan or a Gal-α(1,3)-Gal glycan. The CMAB009 antibody does contain glycans associated with CHO cell expression, including, for example, a Gal-α(2, 3/6)-Gal glycan.

As used herein, the term "in combination" when used in reference to administration of therapies refers to the use of two or more therapeutic agents, e.g., CMAB009 and irinotecan, to treat a disorder, e.g., metastatic colorectal cancer. The use of the term "in combination" does not restrict the order in which therapies are administered to a subject with cancer. For example, a first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject who has had or has cancer. Any additional therapy can be administered in any order with the other additional therapies.

The invention is based on the use of CHO cells to produce an improved anti-EGFR antibody that is more effective and safer than anti-EGFR antibodies produced in, for example, myeloma cells. The glycosylation mechanism in CHO cells is very similar to the IgG glycosylation mechanism in human, earlier studies suggest that the CHO cells lack biosynthetic mechanism of α-Gal epitope-containing glycoprotein, recent studies have reported the presence of α1,3 half galactosidase transferase gene in CHO cells, but it is at no or low expression state during the clone selection process, and it is unclear how this glycoside is α1,3-galactosidase transferase gene is activated in CHO cell line, presumably it associated with the transfection process, similar to other glycoside transferases. Based on this, we designed and selected CHO expression system and successfully prepared genetically engineered anti-EGFR antibody (CMAB009 mAb) with different glycan structures. By structure analysis, it was confirmed the Erbitux® glycan contains a lot of α-Gal, and mostly NGNA as the terminal sialic acid, which has very high immunogenicity. CMAB009 mAb glycan does not contain α-Gal, and terminal sialic acid is mainly in the form of NANA. Subsequent clinical studies have confirmed that the antibody has a good tolerance, with no drug-related hypersensitivity observed, no IgE specific ADA detected. At the same time of greatly reduced immunogenicity, the characteristics of CMAB009 monoclonal antibody in vivo clearance is in line with the in vivo metabolic of chimeric antibodies, and the pharmacokinetic parameters are consistent with those of Erbitux®. CMAB009 monoclonal antibody has initially achieved significant clinical efficacy, and is expected to bring the greatest benefits to potential patients of with hypersensitivity.

Compared with Erbitux® monoclonal antibody, CMAB009 monoclonal antibody has the same amino acid primary structure, while does not contain α-Gal, and the terminal sialic acid is mainly the common human sialic acid form of N-acetylneuraminic acid (NANA). This is consistent with the better tolerance we observed in clinical studies, while no drug-related hypersensitivity observed. At the same time of greatly reduced immunogenicity, the characteristics of CMAB009 monoclonal antibody in vivo clearance is in line with the in vivo metabolic of chimeric antibodies, and the pharmacokinetic parameters are consistent with those of Erbitux®.

This study demonstrates that, it is effective to reducing the immunogenicity of monoclonal antibodies to prevent the occurrence of hypersensitivity, by modifying mAb glycosylation structure, while not affecting the biological activity and clearance characteristics of monoclonal antibody. This can reduce the incidence of clinical adverse reactions, and is expected to bring the greatest benefits to potential patients of hypersensitivity, and provide potential safe, tolerable and effectively targeting drugs.

EXAMPLES

The following embodiments, examples of the present invention are described in further details. However, it should be understood that these embodiments, examples are for illustration purposes only, but not intended to limit the invention.

Example 1: Construction of Eukaryotic Expression Vector

Preferred codons of Chinese hamster were chosen for making most efficient eukaryotic expression vector, so as to obtain more efficient expression in Chinese hamster ovary expression system. Hamsters preferred codons are shown in Table 1.

TABLE 1

Chinese hamster preferred codons

| amino acid | triplet | fraction | Frequency per thousand | number |
|---|---|---|---|---|
| G | GGC | 0.34 | 21.3 | 3268 |
|   | GGA | 0.25 | 15.8 | 2425 |
|   | GGG | 0.21 | 13.4 | 2063 |
|   | GGU | 0.20 | 12.8 | 1968 |
| A | GCC | 0.37 | 25.9 | 3973 |
|   | GCU | 0.32 | 22.4 | 3432 |
|   | GCA | 0.23 | 16.3 | 2497 |
|   | GCG | 0.07 | 5.0 | 765 |
| V | GUG | 0.46 | 30.1 | 4628 |
| L | GUC | 0.24 | 15.7 | 2408 |
|   | GUU | 0.18 | 11.6 | 1780 |
|   | GUA | 0.12 | 7.8 | 1202 |
|   | CUG | 0.39 | 38.8 | 5955 |
|   | CUC | 0.19 | 18.4 | 2818 |
|   | UUG | 0.14 | 14.1 | 2169 |
|   | CUU | 0.13 | 13.2 | 2023 |
|   | CUA | 0.08 | 7.6 | 1174 |
|   | UUA | 0.06 | 6.4 | 978 |
| I | AUC | 0.51 | 24.8 | 3808 |
|   | AUU | 0.35 | 17.4 | 2673 |
|   | AUA | 0.14 | 6.9 | 1053 |
| F | UUC | 0.53 | 22.0 | 3381 |
|   | UUU | 0.47 | 19.6 | 3005 |
| P | CCC | 0.32 | 17.0 | 2608 |

Signal peptide is selected from Chinese hamster B cell antigen receptor complex associated protein β chain. MAT-MVPSSVPCHWLLFLLLLFSGSS (SEQ ID NO: 13), ATG GCC ACC ATG GTG CCC TCT TCT GTG CCC TGC CAC TGG CTG CTG TTC CTG CTG CTG CTG TTC TCT GGC TCT TCT (SEQ ID NO: 14).

Designed and synthesized according to the most preferred codons of Chinese hamster, the CMAB009 light chain comprises the nucleotide sequence of SEQ ID NO: 1 and the amino acid sequences of SEQ ID NO: 2, the CMAB009 heavy chain comprises the nucleotide sequence SEQ ID NO: 3 and the amino acid sequence SEQ ID NO 4. The said light chain and heavy chain above were ligated into the highly efficient Eukaryotic cell expression vector to obtain the light chain and heavy chain Eukaryotic expression vector.

Example 2: Selection and Engineering of the Host Cell

In the biopharmaceutical field selection of host cells needs to focus on several important aspects: glycosylation and other post-translational modifications types to avoid causing immunogenicity; host cells suitable for large-scale cultivation in bioreactors, and can grow to high density in chemically defined and animal component free (ACDF) medium; virus safety; suitable for cloning and pressure screening in the ACDF.

CHO cell can grow at high density in bioreactors, is easy for genetic manipulation, has N-glycosylation similar to humans, lower the risk of virus transmission, and is widely used in the biopharmaceutical field. The most commonly used clone for industrial production is the CHO-K1, CHO-DXB11 and CHO-DG44. CHO-K1 is similar to the primary CHO cell, while DG44 and DXB11 were manipulated through random mutagenesis to remove DHFR gene, so they can be used for gene amplification via metabolic defects. CHO-K1 uses CS selection system, but has a lower screening efficiency because of the endogenous CS expression in CHO-K1.

The present invention chose the more widely used CHO cells as host cells which are more suitable for industrial production of therapeutic antibodies, and performed proper engineering of CHO-K1. We used CRTSPR/Cas techniques to knockout the CS gene of CHO-K1, and obtained cell line designated as CHO-CR-GS$^{-/-}$, eliminating the expression of the endogenous CS, which is therefore more beneficial for screening of high expression cell clones.

Example 3: Transfecting Host Cells and Screening High Expression Clones

Liposome based cotransfection of CHO-CR-GS$^{-/-}$, screening under the pressure of CS selection system were performed to obtain stable cell clones with highly efficient expression of anti-EGFR monoclonal antibody. After several rounds of transfection and screening, cell clones were obtained with expressing amount greater than 20 pg/cell·day.

Example 4: Identification of Culture Conditions

We have developed universal basal medium for CHO-CR-G5$^{-/-}$, which is chemically defined type of medium (Chemical Defined, CD), i.e. the medium is made by combining amino acids, vitamins, inorganic salt, glucose and trace elements according to cell growth needs and certain percentages. This basal medium can meet the initial growth needs of the engineered cells obtained from screening. In order to further improve the desired antibody yield from the engineered cells, optimizations were performed for the basal medium, including adding hormones, genetically engineered recombinant growth factors, adjusting amino acids amounts.

The culture PH is: 6.5~6.9, preferably pH6.6; culture temperature is: 33° C.~36° C., preferably 34° C.; osmolality is: 290 mOsm/kg~350 mOsm/kg, preferably 340 mOsm/kg.

After multiple comparisons and optimization, the culture (CHOM-B09) and supplemented medium (CHOM-S09) were ultimately determined suitable for the large scale serum-free culture of the engineered cells expressing anti-EGFR monoclonal antibody, with culture conditions: pH6.6, temperature 34° C., and osmotic pressure of 340 mOsm/kg.

The expression yield of the engineered cells is greater than 30 pg/cell·day in the optimized medium, using Fed-batch culture mode. The yield of the desired antibody may be greater than 3 g/L in the culture supernatant harvested after 2 weeks of culture period.

Example 5: Purification and Isolation of CMAB009 Antibody

The high expression clone obtained from the screening was cultured in expanded scale with serum-free culture medium, supernatant was collected, centrifuged at 9000 rpm*20 min, 4° C., pellet and the cell debris was discarded. concentrated by ultrafiltration using ultrafiltration packets of 50 KB membrane from Millipore Corporation, then centrifuged at 9000 rpm*30 min, 4° C. to remove cell debris, filtered with 0.45 um membrane, used rProtein A (recombinant protein a) by affinity chromatography to do preliminary purification, in-situ wash buffer is 6M GuCl, the binding buffer for the column is 20 mM PB+150 mM NaCl pH7.0, after balancing with three to five column volumes, using three to five column volumes of elution buffer 20 mM Citric Acid (citrate buffer) pH3.0 to elute. Column is stored in 20% EtOH after equilibration and washing. The eluted desired protein from rProteinA was desalted and buffer exchanged using Hitrap G25 (GE Healthcare), the column elution buffer is PBS (20 mM PB+150 mM NaCl pH7.0), in-situ washing solution is 0.5M NaOH. All of the above purification steps were performed on ice, the antibodies obtained from purification were concentrated with 50 KD ultrafiltration centrifuge tubes (Merck Millipore) and to give CMAB009 monoclonal antibody.

Figure 7:
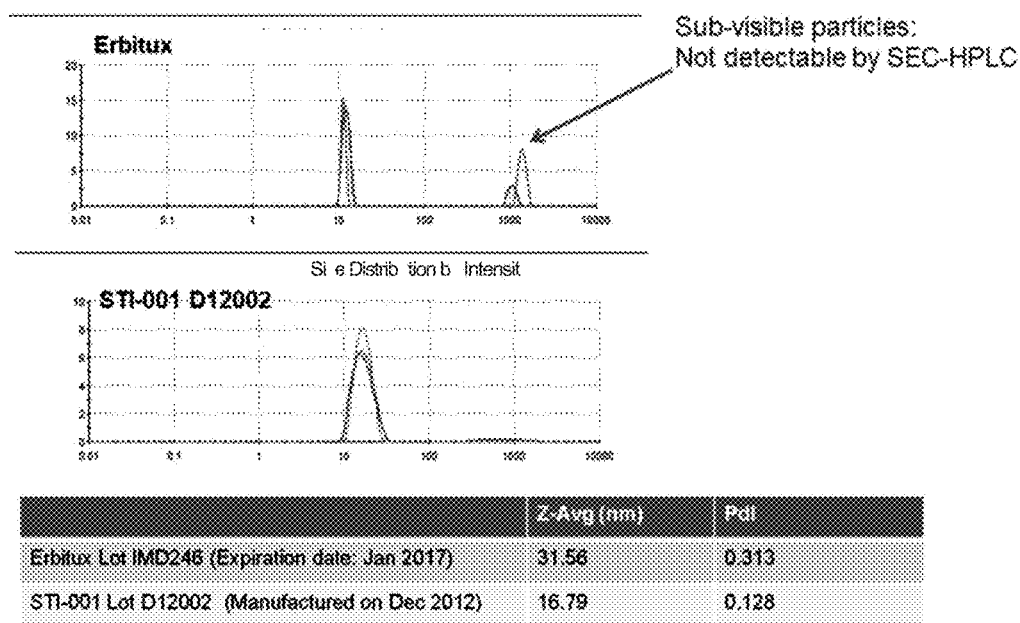
FIG. 7 graphically depicts characterization of CMAB009 versus Erbitux® using DLS methods to determine size distribution.

Following purification, CMAB009 was characterized according to standard dynamic light scattering (DLS) analysis. It was determined that CMAB009 has a more homogenous size distribution in comparison to Erbitux®. The z-average (z-avg) for Erbitux® was determined to be 31.56 nm, while the z-avg. for CMAB009 was 16.79 nm. Furthermore, the polydispersity index (PDI) of Erbitux® was determined to be 0.313, versus 0.128 for CMAB009. The characterization of CMAB009 versus Erbitux® using DLS methods to determine size distribution was shown in FIG. 7.

Example 6: Comparison of the Glycosylation of the Culture Product

LC/MS, MS/MS techniques were used for the comparative analysis of the sugar chains of CMAB009 monoclonal antibody and Cetuximab (Erbitux®, C225 monoclonal antibody).

Sample preparation: Fc fragment and oligosaccharide from Fab were prepared after glucosidase digestion; oligosaccharides exonuclease treatment of oligosaccharides on Fab; 2-AB fluorescence labeling of oligosaccharides; After HILIC solid phase extraction to remove excess 2-AB, oligosaccharides were obtained with fluorescence labeled sugar chains, then analyzed via LC/MS and MS/MS chromatography.

Figure 2:
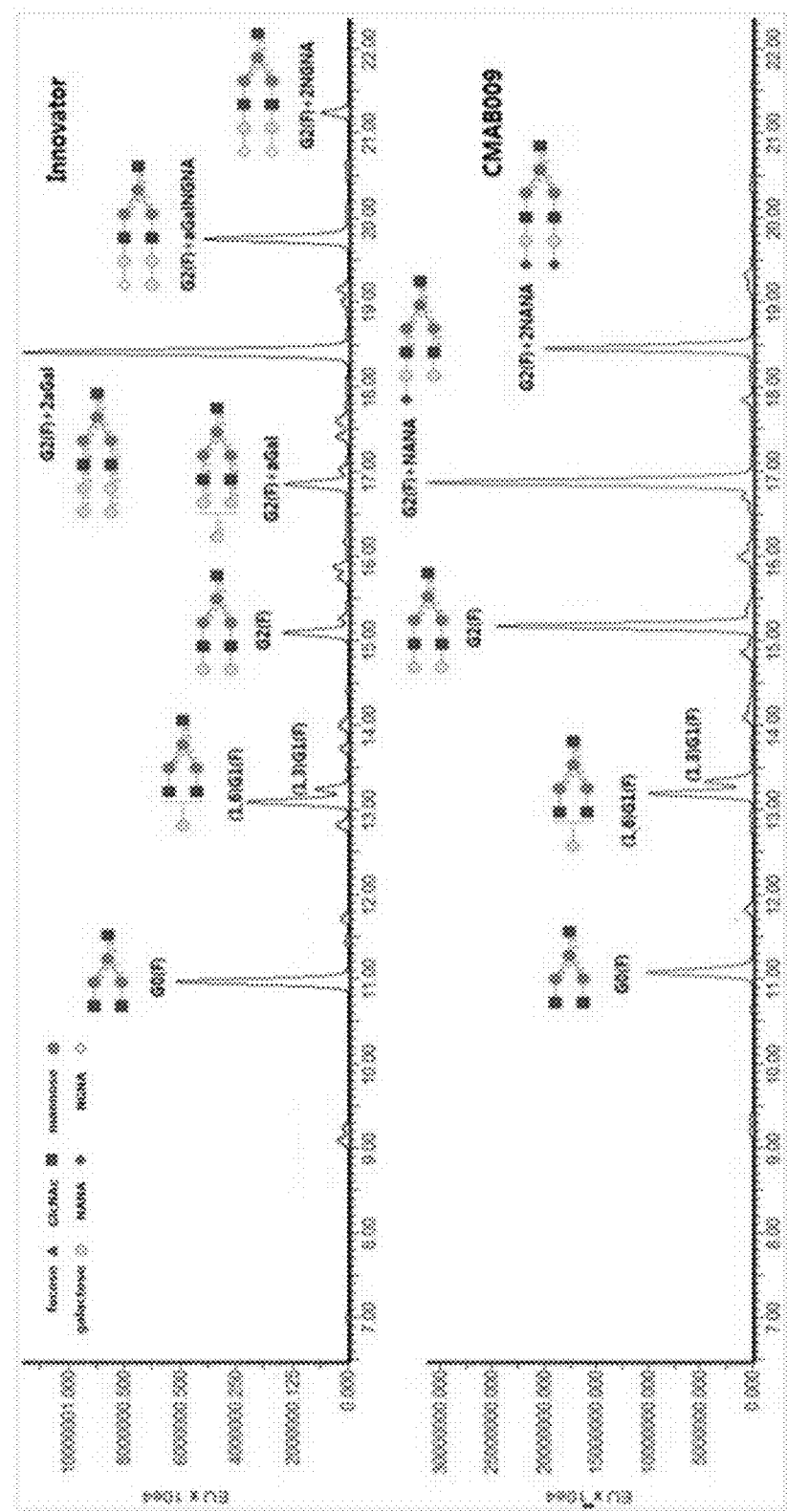

The free glycans from glycosidase treatment of MAb, after fluorescent labeling, will be analyzed respectively by LC/MS, MS/MS and oligosaccharide exonuclease treatment. The results show that, CMAB009 antibody and the original antibody Cetuximab (Erbitux®) each have two glycosylation sites, with exactly the same glycan chain structure on their Fc segments, results in FIG. 1. But Fab segments have different glycan chain structures, with mostly the sialic acid NANA glycan chain structure on CMAB009 Fab fragment, and mostly the sialic acid NGNA glycan chain structure on original Cetuximab Fab fragment; The glycans of CMAB009 Fab do not contain α-galactose, while the glycans of original Cetuximab Fab contain a large amount of α-galactose. LC/MS analysis of the glycan structure of the heavy chain Fab fragment is shown in FIG. 2.

Example 7: Clinical Tolerance Study

Initial Evaluation of CMAB009 mAb Clinical Tolerance

An initial study enrolled a total of 18 subjects, with 3, 6, 6 subjects each assigned to dose groups of 100 mg/m$^2$ dose, 250 mg/m$^2$ dose and 400 mg/m$^2$ dose, respectively, in the study of single intravenous administration. Among the subjects enrolled in single dose study, 3 subjects withdrew due to disease progression, according to the study design the remaining 15 subjects multiple administration inclusion criteria were enrolled in the multiple dose group meeting, with 3 extra subjects were enrolled to multiple dose (Table 1)

TABLE 1

Allocation of patients to the different dose groups

| Patient No. | Single-dose phase | Multiple-dose phase |
|---|---|---|
| #01 | 100 mg/m$^2$ | Group A |
| #02 | 100 mg/m$^2$ | Disease progression |
| #03 | 100 mg/m$^2$ | Group A |
| #04 | 250 mg/m$^2$ | Group A |
| #05 | 250 mg/m$^2$ | Group A |
| #06 | 250 mg/m$^2$ | Group A |
| #07 | 250 mg/m$^2$ | Group A |
| #08 | 250 mg/m$^2$ | Group A |
| #09 | 250 mg/m$^2$ | Group B |
| #10 | 400 mg/m$^2$ | Group B |
| #11 | 400 mg/m$^2$ | Disease progression |
| #12 | 400 mg/m$^2$ | Group B |
| #13 | 400 mg/m$^2$ | Group B |
| #14 | 400 mg/m$^2$ | Disease progression |
| #15 | 400 mg/m$^2$ | Group B |
| #16 | — | Group B |
| #17 | — | Group B |
| #18 | — | Group B |

Subjects enrolled in this study were refractory to effective conventional treatment methods, experienced failure from conventional treatment or patients with relapse of advanced cancers, including 10 cases of colorectal cancer, 7 cases of lung cancer, 1 case of gastric cancer, the demographic statistical characteristics and prior treatment of the subjects are shown in Table 2.

TABLE 2

Patient characteristics

| | No. patients |
|---|---|
| Total | 18 |
| Treated on fixed dose extension phase | 14 |
| Median age, y(range) | 52 (29-64) |
| Sex | |
| Male | 9 |
| Female | 9 |
| Tumor type | |
| Colorectal | 10 |
| NSCLC | 7 |
| Gastric | 1 |
| No. prior chemotherapy regimens | |
| 2 | 7 |
| 3 | 4 |
| ≥3 | 4 |
| Radiotherapy | 7 |

Comparison and analysis were performed on subjects' baselines, and the age, height, weight, body surface, ECOG score of subjects from the three groups of single dose and the two groups of multiple doses. The results are shown in Table 3 with no statistically significant difference.

TABLE 3

Subject characterstics at baseline. Mean ± SD

| Characterstic | Single-dose phase | | | Multiple-dose phase | |
| --- | --- | --- | --- | --- | --- |
| | 100 mg/m² (n = 3) | 250 mg/m² (n = 6) | 400 mg/m² (n = 6) | Group A (n = 7) | Group B (n = 8) |
| Age (years) | 58.00 (49.00-58.00) | 55.00 (49.00-58.00) | 55.50 (49.00-58.00) | 57.00 (49.00-58.00) | 54.00 (49.00-58.00) |
| Height (cm) | 161.00 (145.00-170.00) | 168.5 (165.00-172.00) | 173.00 (160.00-176.00) | 165.00 (152.00-172.00) | 171.00 (160.00-175.00) |
| Weight (kg) | 54.00 (37.00-58.00) | 67.50 (67.00-70.00) | 63.50 (54.00-81.00) | 67.00 (46.00-71.00) | 66.50 (61.75-76.00) |
| BSA (m²) | 1.55 (1.20-1.67) | 1.75 (1.70-1.80) | 1.75 (1.50-1.90) | 1.74 (1.40-1.81) | 1.76 (1.61-1.87) |
| ECOG | 1.00 (1.00-2.00) | 1.00 (1.00-1.00) | 1.00 (1.00-1.00) | 1.00 (1.00-2.00) | 1.00 (1.00-1.00) |

The results showed that the CMAB009 monoclonal antibody was well tolerated. Among the 18 subjects, there was no grade III-IV drug-related toxicity as showed in Table 4, with all occurring drug-related toxicity at grade I-II, and the incidence of toxicity was independent of the doses or the dosing frequency. No dose-limiting toxicity was observed, and no drug-related hypersensitivity was observed.

TABLE 4

CMAB009-related toxicities

| N = 18 | CTC Grade | | | Total no. events | % |
| --- | --- | --- | --- | --- | --- |
| | I | II | III-IV | | |
| Acne-like rash | 10 | 1 | 0 | 11 | 61.1 |
| Fever chills | 6 | 4 | 0 | 10 | 55.6 |
| Nausea/vomiting | 5 | 0 | 0 | 5 | 27.8 |
| Headache | 3 | 0 | 0 | 3 | 16.7 |
| Fatgue/malaise | 1 | 0 | 0 | 1 | 5.6 |
| Transaminase elevation | 1 | 0 | 0 | 1 | 5.6 |
| paronychia | 1 | 0 | 0 | 1 | 5.6 |
| Nasal discharge | 1 | 0 | 0 | 1 | 5.6 |

There was no CMAB009 antibody related hypersensitivity observed in this study, while the findings by Paula M. Fracasso and others indicated that the incidence of hypersensitivity reactions associated with Erbitux® reached 31%, of which class III-IV hypersensitivity incidence is 13%. Christine H. Chung and others conducted research on the hypersensitivity occurring in administering of original Erbitux® (Chung C H, Mirakhur B, et al. Cetuximab-induced anaphylaxis and IgE specific for galactose-alpha-1, 3-galactose. N Engl J Med 2008; 358 (11): 1109-17). Among 76 subjects who received Erbitux® treatment, 25 subjects had hypersensitivity, with hypersensitivity incidence reached 33%, which is consistent with the results by Paula M. Fracasso. Christine H. Chung's study confirmed Erbitux® related hypersensitivity is α-Gal-specific IgE-mediated.

Example 8: Clinical Result Safety, Immunogenicity Study

CMAB009 monoclonal antibody clinical safety: most adverse events were drug-related rash, there were no clinically significant new toxicity observed, and there no was severe hypersensitivity observed among the 73 subjects.

Immunogenicity is an important aspect in biopharmaceutical safety assessment. Traditional ELISA can be used for immunogenicity analysis, but the problem is, theoretically, the coated Fab segments for capturing antibody should be oriented to the optimal confirmation to facilitate the antigen-antibody interaction, the Fab fragments for capturing sometimes are partially or entirely bound to microtiter plates, which results in the reduction of antibody capturing activity.

In this study, the biosensors made with biofilm interference technology and optical fibers were employed, in which the bottom was covered with SA ligands conjugated with biomolecule compatible layers. Once the captured biotinylated antibody is bound to the ligands, the biofilm thickness increases, reflected light interference spectral curve drift a measurable distance, thereby enabling real-time measurement of intermolecular interactions. This method is equivalent to the self-assembly process of the captured antibodies, which formed a range of optimal conformations at a certain density for capturing antibody on the surface of the biosensor, which not only improves the analytical sensitivity but also increases the linear range, which helps reduce the false-positive reactions from non-specific binding.

Figure 3:
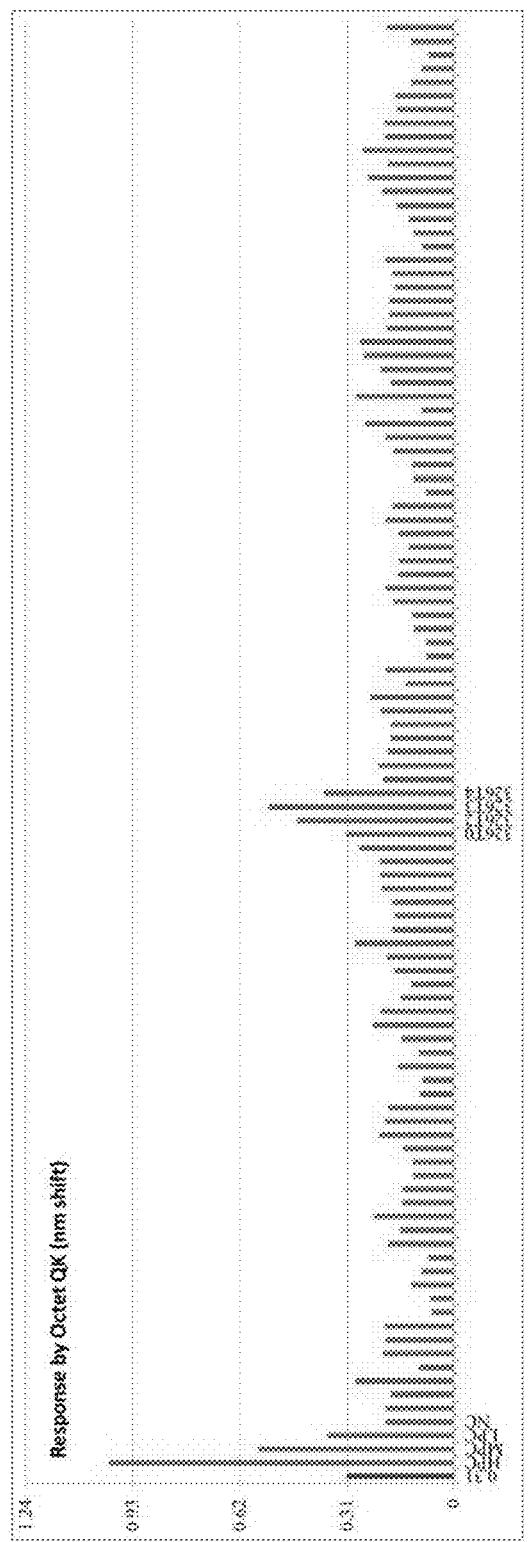
Figure 4:
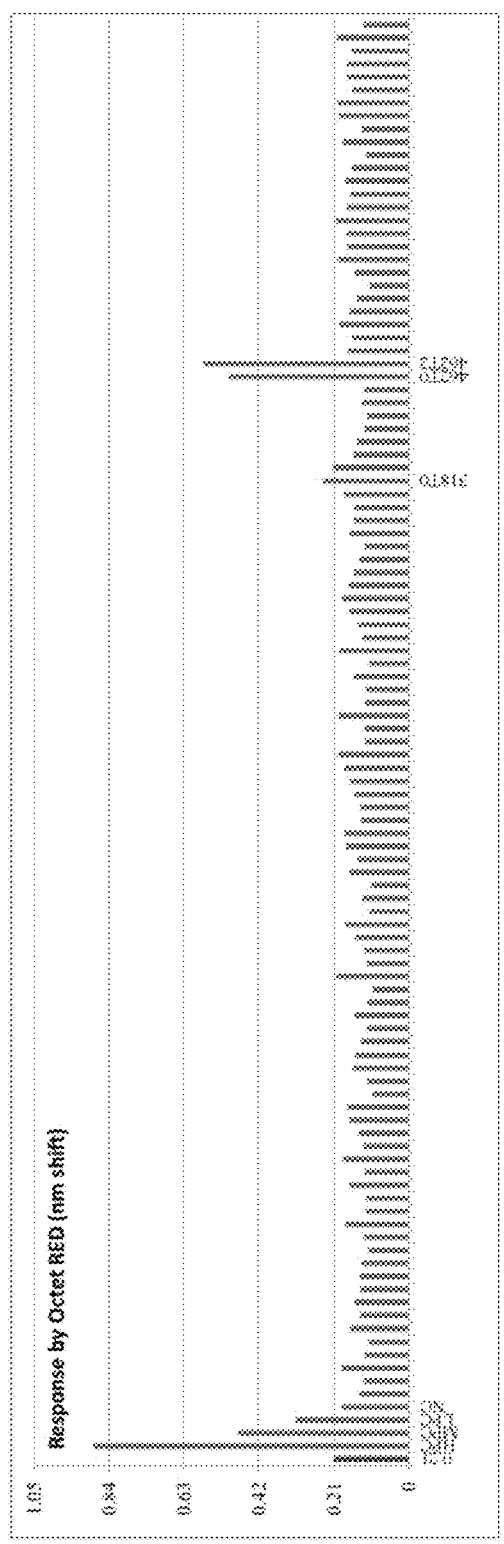
FIG. 4 Fortebio Octet immunogenicity analysis (Octet RED System)

Fortebio Octet immunogenicity analysis: examination of ADA in clinical serum samples, the results shown in FIG. 3, 4: cut point value analysis showed that there were 3 subjects of potentially positive in 73 subjects (HPC highly positive, MIPC is positive, LPC is low positive, NC negative).

As to the immunogenicity analysis of CMAB009 monoclonal antibody in this study, the results showed that there was ADA detected in 1.4% (1/73) of the subjects, with IgG type confirmed by subtype analysis, which are not the IgE type ADA mediated by hypersensitivity. The results of this study is consistent with the results of clinical safety evaluation, since there was no severe hypersensitivity reactions observed among subjects in clinical studies.

Example 9: CMAB009 Treatment Results in Improved Efficacy for Treating Cancer and Reduced Immunogenicity CMAB009 was administered to patients having metastatic colorectal cancer in a Phase 2/3 study to determine the efficacy and immunogenicity of CMAB009. As described below, the results from the study were then compared to similar studies performed using Erbitux® (cetuximab). Surprisingly, it was determined that CMAB009 has additional efficacy beyond that known for Erbitux®. For example, CMAB009 was able to increase the overall survival and length of time to disease progression in patients. The below study is comparable to the Erbitux® (cetuximab) study described in Alberto F. Sobrero, et al. Clin Oncol, 2008, 26:2311-2319.

The CMAB009 study was initiated by screening patients to identify those with 1) histological confirmed metastatic colorectal adenocarcinoma, 2) KRAS wild-type tumors, EGFR-expressing or EGFR-noexpressiong by immunohistochemistry, 3) has measurable lesion, at least 1 cm in diameter by CT or Mill, at least 2 cm diameter by physical examination or other iconography, 4) ECOG performance status 0 to 1, 5) failure (disease progression/discontinuation due to toxicity) of fluoropyrimidine and oxaliplatin treatment, stop at least one month thereafter, irinotecan-naïve. 501 patients were identified and randomized in a 2:1 manner to group 1 or group 2. Group 1 included 337 patients who were administered a combination of CMAB009 and irinotecan. Specifically, the patients in group 1 were administered an initial dose of 400 mg/m$^2$ of CMAB009 followed by weekly infusions of 250 mg/m$^2$ thereafter. Irinotecan doses were maintained 180 mg/m2 every 2 weeks. Group 2 included 164 patients who were administered irinotecan monotherapy at a dose consistent with the patient's therapy prior to the study. Patients in both groups were treated until the disease progressed or the patient reached an unacceptable level of toxicity. Patient baseline characteristics are provided in Table 5.

TABLE 5

Baseline characteristics

| | CMAB009 Ph2/3 trial | |
|---|---|---|
| | CMAB009 +irinotecan (n = 337) | Irinotecan monotherapy (n = 164) |
| Age(yr) | | |
| Median | 55 | 55 |
| Range | 20-72 | 20-71 |

TABLE 5-continued

Baseline characteristics

| | CMAB009 Ph2/3 trial | |
|---|---|---|
| | CMAB009 +irinotecan (n = 337) | Irinotecan monotherapy (n = 164) |
| Sex-no. (%) | | |
| Male | 195 (57.9) | 104 (63.4) |
| Female | 142 (42.1) | 60 (36.6) |
| Race-no. (%) | | |
| White | 0 | 0 |
| Black | 0 | 0 |
| Asian | 334 (99.1) | 159 (97.0) |
| Others | 3 (0.9) | 5 (3.0) |

Patients were evaluated for radiologic response in both group 1 and group 2. The results are described in Table 6. Note the overall response rate (ORR) in Table 6 was determined according to the sum of the rate of CR and PR, and the disease control rate (DCR) was determined according to the sum of the rates of CR, PR, and SD.

When compared to data reported for Erbitux® (cetuximab) from a similar study (see Alberto F. Sobrero, et al. Clin Oncol, 2008, 26:2311-2319), patients receiving CMAB009 showed better overall survival (10.7 months for patients receiving Erbitux® (cetuximab)+irinotecan vs. 17.6 months for patients receiving CMAB009+irinotecan) and an increased time to disease progression (4.0 months for patients receiving Erbitux® (cetuximab)+irinotecan vs, 5.6 months for patients receiving CMAB009+irinotecan).

TABLE 6

Radiologic response of CMAB009 compared with Erbitux ®

| | Erbitux ® Ph3 trial (EPIC) | | | CMAB009 Ph2/3 trial | | |
|---|---|---|---|---|---|---|
| | Cetuximab + irinotecan (n = 648), | Irinotecan monotherapy (n = 650) | P-value | CMAB009 + irinotecan (n = 337) | Irinotecan monotherapy (n = 164) | P-value |
| Complete response | 9 (1.4) | 1 (0.2) | | 4 (1.2) | 1 (0.6) | |
| Partial response | 97 15.0) | 26 (4.0) | | 107 (31.8) | 20 (12.2) | |
| Stable disease | 292 (45.1) | 271 (41.7) | | 159 (47.2) | 86 (52.4) | |
| Progressive disease | 174 (26.9) | 243 (37.4) | | 47 (13.9) | 44 (26.8) | |
| Unable to evaluate | 56 (8.6) | 72 (11.1) | | 20 (5.9) | 13 (7.9) | |
| Overall response rate | 106 (16.4 [13.6-19.41]) | 27 (4.2 [2.8-6.01]) | <0.001 | 111 (32.9 [27.9-38.2]) | 21 (12.8 [8.1-18.9]) | <0.001 |
| Disease control rate | 398 (61.4) | 298 (45.8) | <0.001 | 270 (80.1 [75.5-84.2]) | 107 (65.2 [57.4-72.5]) | 0.0004 |
| Overall survival (months) | 10.7 | 10.0 | | 17.5 | 16.8 | |
| Time to disease progression (months) | 4.0 | 2.6 | | 5.6 | 3.2 | |

Figure 5:
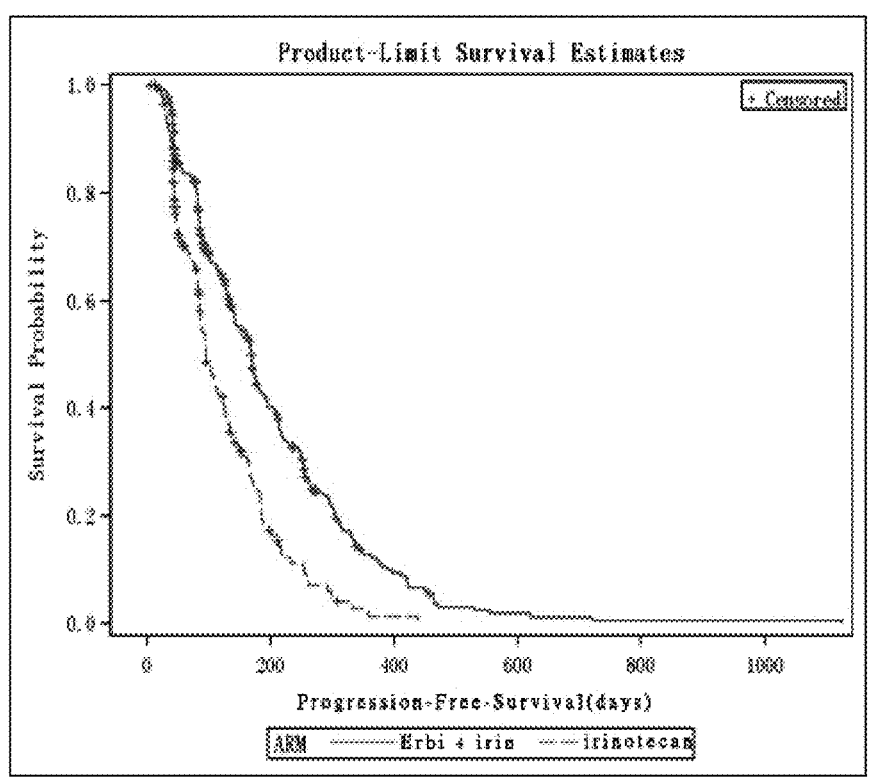
FIG. 5 graphically depicts the progression free survival (PFS) in the CMAB009 study described in Example 9. PFS is defined as the time from randomization until objective tumor growth progression or death.
Figure 6:
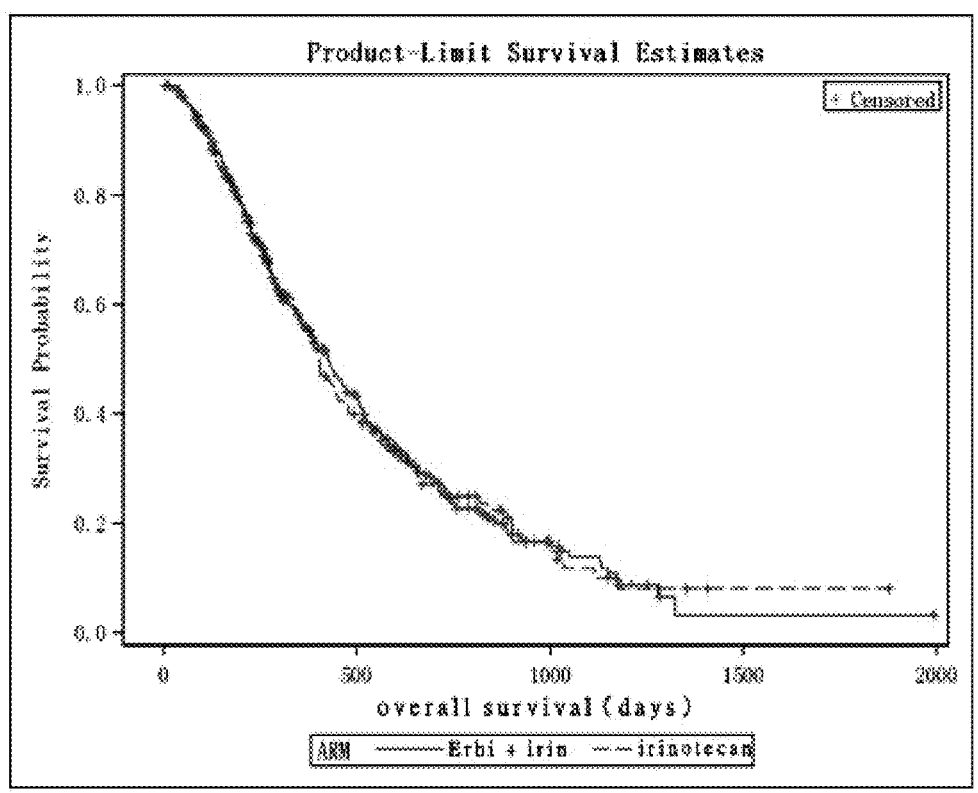
FIG. 6 graphically depicts overall survival (OS) of patients in the CMAB009 study described in Example 9.

When compared to reported data for Erbitux®, surprisingly the overall survival of the patients was greater in the patients receiving CMAB009, i.e., 10.7 months for Erbitux® (cetuximab)+irinotecan vs. 17.5 months for CMAB009+irinotecan. Data showing an increase in disease progression from this CMAB009 study is also provided in FIG. 5 (compare to published Erbitux® (cetuximab) data; see FIG. 3 of Alberto F. Sobrero, et al. Clin Oncol, 2008, 26:2311-2319. Data showing an increase in overall survival from this CMAB009 study is also provided in FIG. 6 (compare to published Erbitux® (cetuximab) data; see FIG. 2 of Alberto F. Sobrero, et al. Clin Oncol, 2008, 26:2311-2319).

A safety evaluation of the study is provided below in Table 7.

TABLE 7

Safety evaluation

|  | Antibody + Irino (N = 342) | Irino (N = 170) | Total (N = 512) | PValue |
|---|---|---|---|---|
| At least one AE | 332 (97.1%) | 148 (87.1%) | 480 (93.8%) | <.0001 |
| At least one ADR | 320 (93.6%) | 126 (74.1%) | 446 (87.1%) | <.0001 |
| At least one important AE | 302 (88.3%) | 120 (70.6%) | 422 (82.4%) | <.0001 |
| At least one Level III or above AE | 38 (11.1%) | 12 (7.1%) | 50 (9.8%) | 0.1458 |
| At least one Level III or above ADR | 27 (7.9%) | 10 (5.9%) | 37 (7.2%) | 0.4076 |
| At least one Level III or above important AE | 37 (10.8%) | 11 (6.5%) | 48 (9.4%) | 0.1119 |
| At least one SAE | 23 (6.7%) | 8 (4.7%) | 31 (6.1%) | 0.3669 |
| At least one test drug-related SAE | 7 (2.0%) | 1 (0.6%) | 8 (1.6%) | 0.2800 |
| At least one AE which lead to stop drug treatment | 73 (21.3%) | 27 (15.9%) | 100 (19.5%) | 0.1420 |
| Test drug-related death AE | 1 (0.3%) | 0 | 1 (0.2%) | 1.0000 |

Notably, adverse events from the CMAB009 study were lower than those reported for Erbitux® (cetuximab). The grade 3-4 adverse events are described below in Table 8 (compare to Table 3 of Alberto F. Sobrero, et al. Clin Oncol, 2008, 26:2311-2319).

TABLE 8

Grade 3-4 adverse events for CMAB009 study

|  | CMAB009 +irinotecan (n = 337) | Irinotecan monotherapy (n = 164) |
|---|---|---|
| Any | 180 (54.2) | 57 (38.9) |
| Anemia | 3 (0.9) | 3 (1.8) |
| Neutropenia | 53 (15.7) | 14 (8.5) |
| Thrombocytopenia | 0 | 0 |
| Diarrhea | 35 (10.4) | 12 (7.3) |
| Asthenia | 19 (5.6) | 6 (3.7) |
| Acne-like rash | 0 | 0 |
| Nausea and vomiting | 16 (4.7) | 16 (9.8) |
| Abdominal pain | 3 (0.9) | 0 |
| Stomatitis | 1 (0.3) | 0 |
| Dyspnea | N/A | N/A |
| Fever | 5 (1.5) | 1 (0.9) |

In sum, despite having the same primary structure, CMAB009 surprisingly was not only more effective than Erbitux® (cetuximab), providing, for example, a longer time to disease progression, but had a reduced rate of adverse events associated with hypersensitivity reactions, e.g., acne-like rash or diarrhea.

The invention claimed is:

1. A composition comprising an antibody, and a pharmaceutically acceptable carrier,
   wherein the antibody comprises a light chain comprising an amino acid sequence set forth in SEQ ID NO: 2 and a heavy chain comprising an amino acid sequence set forth in SEQ ID NO: 4, and
   wherein the antibody has a z-average (z-avg) of 10-25 nm as determined by a dynamic light scattering (DLS) analysis,
   wherein the Fab segments of the antibody have a sialic acid NANA glycan chain structure, and
   wherein the antibody does not comprise an N-glycolylneuraminic acid (NGNA) and does not comprise a Gal-α(1,3)-Gal glycan,
   wherein the antibody binds epidermal growth factor receptor (EGFR).

2. The composition of claim 1, wherein the antibody is produced by a method comprising:
   a) providing an anti-EGFR monoclonal antibody comprising a light chain comprising the amino acid sequence of SEQ ID NO: 2 and a heavy chain comprising the amino acid sequence of SEQ ID NO: 4;
   b) constructing a recombinant plasmid using a nucleic acid encoding the light chain and the heavy chain,
   c) transfecting CHO cells with the recombinant plasmid;
   d) screening for a high-expressing clone;
   e) culturing in large scale, the high-expressing clone, wherein a cell culture temperature is 33° C.~36° C., a pH of a cell culture growth media is 6.5~6.9, and an osmotic pressure of the cell culture growth media is 290 mOsm/kg~350 mOsm/kg;
   f) isolating the cultured clone of e); and
   g) purifying the isolated clone of f) to obtain the anti-EGFR monoclonal antibody.

3. The composition of claim 2, wherein the cell culture temperature is 34° C.

4. The composition of claim 2, wherein the pH of the cell culture growth media is pH 6.6.

5. The composition of claim 2, wherein the osmotic pressure of the cell culture growth media is 340 mOsm/kg.

6. A liquid pharmaceutical composition comprising water and an anti-EGFR antibody, wherein the anti-EGFR antibody comprises a light chain comprising the amino acid sequence set forth in SEQ ID NO: 2 and a heavy chain comprising the amino acid sequence set forth in SEQ ID NO: 4,
   wherein the antibody has a z-average (z-avg) of 10-25 nm as determined by dynamic light scattering (DLS) analysis, and the anti-EGFR antibody does not comprise an N-glycolylneuraminic acid (NGNA), and does not comprise a Gal-α(1,3)-Gal glycan.

7. The composition of claim 6, wherein the z-avg of the antibody is 15-20 nm.

8. The composition of claim 6, wherein the antibody is produced by a method comprising:
   a) providing an anti-EGFR monoclonal antibody, the anti-EGFR monoclonal antibody comprising a light chain comprising the amino acid sequence of SEQ ID NO: 2 and a heavy chain comprising the amino acid sequence of SEQ ID NO: 4;
   b) constructing a recombinant plasmid using a nucleic acid encoding the light chain and the heavy chain,
   c) transfecting CHO cells with the recombinant plasmid;
   d) screening for a high-expressing clone;
   e) optimizing cell culture conditions, culturing in large scale, the high-expressing clone from d), wherein the cell culture growth media is maintained at a temperature of 33° C.~36° C. at a pH of 6.5~6.9 and wherein the osmotic pressure of the cell culture growth media is 290 mOsm/kg~350 mOsm/kg;
   f) isolating the cultured clone of e); and
   g) purifying the isolated clone of f) to obtain the antibody.

9. The composition of claim 8, wherein the cell culture temperature is 34° C.

10. The composition of claim 8, wherein the pH of the cell culture growth media is pH 6.6.

11. The composition of claim 8, wherein the osmotic pressure of the cell culture growth media is 340 mOsm/kg.

12. A liquid pharmaceutical composition comprising water and an anti-EGFR antibody,
   wherein the anti-EGFR antibody comprises a light chain comprising the amino acid sequence set forth in SEQ ID NO: 2 and a heavy chain comprising the amino acid sequence set forth in SEQ ID NO: 4,
   wherein the anti-EGFR antibody is produced in a Chinese Hamster Ovary (CHO) cell,
   and wherein the composition does not comprise a polysorbate and/or a saccharobiose.

13. A liquid pharmaceutical composition consisting essentially of water, an anti-EGFR antibody, sodium chloride, sodium dihydrogen phosphate dihydrate, and disodium phosphate dihydrate,
   wherein the anti-EGFR antibody comprises a light chain comprising the amino acid sequence set forth in SEQ ID NO: 2 and a heavy chain comprising the amino acid sequence set forth in SEQ ID NO: 4, and
   wherein the anti-EGFR antibody does not comprise an N-glycolylneuraminic acid (NGNA) glycan, does not comprise a Gal-α(1,3)-Gal glycan, and/or does comprise a Gal-α(2, 3/6)-Gal glycan.

14. A method of producing an anti-EGFR monoclonal antibody, said method comprising:
   a) an anti-EGFR monoclonal antibody comprises a light chain comprising the amino acid sequence of SEQ ID NO: 2 and a heavy chain comprising the amino acid sequence of SEQ ID NO: 4;
   b) constructing a recombinant plasmid using a nucleic acid encoding the light chain and the heavy chain;
   c) transfecting CHO cells with the recombinant plasmid;
   d) screening for a high-expressing clone;
   e) culturing in large scale, the high-expressing clone, wherein a cell culture temperature is 33° C.~36° C., a pH of a cell culture growth media is 6.5~6.9, and an osmotic pressure of the cell culture growth media is 290 mOsm/kg~350 mOsm/kg;
   f) isolating the cultured clone of e); and
   g) purifying the isolated clone of f) to obtain the anti-EGFR monoclonal antibody.

15. The method of claim 14, wherein the coding sequences for the light chain and heavy chain of the anti-EGFR monoclonal antibody are designed and synthesized according to the codons preference of Chinese hamster ovary cells.

16. The method of claim 14, wherein said host cell is a mammalian CHO cell.

17. The method of claim 14, wherein said cell culture temperature is 33° C.~36° C., preferably 34° C.

18. The method of claim 14, wherein said pH of the cell culture growth media is 6.5~6.9.

19. The method of claim 14, wherein said osmotic pressure of the cell culture growth media is 290 mOsm/kg~350 mOsm/kg.

20. The method according to claim 17 wherein the cell culture growth media is serum-free cell culture growth media, and the host cell is cultured in serum-free conditions.

21. The antibody of claim 14 wherein said antibody has lower immunogenicity than the antibodies produced with currently existing.

22. A method according to claim 14 further comprising the step of administering in combination with other drugs for treating tumors expressing epidermal growth factor receptor (EGFR).

23. A method of inhibiting progression of cancer in a human subject, said method comprising administering the composition of claim to the subject, such that progression is inhibited.

24. A method of treating a human subject having cancer, said method comprising administering the composition of claim 6 to the subject, such that the cancer is treated.

25. The method of claim 24 wherein the cancer is squamous cell carcinoma of the head and neck (SCCHN) or colorectal cancer.

26. The method of claim 25, wherein the colorectal cancer is K-Ras wild-type, EGFR-expressing colorectal cancer.

27. The method of claim 26, wherein the antibody is administered in combination with FOLFIRI (Folinic Acid, Fluorouracil and Irinotecan Hydrochloride).

28. The method of claim 26, wherein the antibody is administered in combination with irinotecan.

29. The method of claim 24 wherein the subject has recurrent or metastatic squamous cell carcinoma of the head and neck and has failed prior platinum-based therapy.

30. The method of claim 24 wherein the subject has locally or regionally advanced squamous cell carcinoma of the head and neck.

31. The method of claim 30, wherein the antibody is administered in combination with radiation therapy for the initial treatment of the cancer.

32. The method of claim 24 wherein the subject has recurrent locoregional disease or metastatic squamous cell carcinoma of the head and neck.

33. The method of claim 29, wherein the antibody is administered in combination with platinum-based therapy with 5-FU.

34. The method of claim 24 wherein the antibody is administered in combination with an additional therapeutic agent.

35. The method of claim 34, wherein the additional therapeutic agent is a chemotherapeutic agent.

36. The method of claim 24 wherein the subject has failed oxaliplatin- and irinotecan-based chemotherapy.

37. The method of claim 24 wherein the subject is intolerant to irinotecan.

38. A method of treating or inhibiting progression of colorectal cancer in a subject having colorectal cancer, said method comprising administering an anti-EGFR antibody and irinotecan, such that colorectal cancer is treated, wherein the antibody comprises a light chain comprising the amino acid sequence set forth in SEQ ID NO: 2, comprises a heavy chain comprising the amino acid sequence set forth in SEQ ID NO: 4, and contains a Gal-α 2, 3/6)-Gal glycan.

39. A method of treating or inhibiting progression of colorectal cancer in a subject having colorectal cancer, said method comprising administering an anti-EGFR antibody and irinotecan, such that colorectal cancer is treated, wherein the antibody comprises a light chain comprising the amino acid sequence set forth in SEQ ID NO: 2, comprises a heavy chain comprising the amino acid sequence set forth in SEQ ID NO: 4, and does not contain either an N-glycolylneuraminic acid (NGNA) glycan or a Gal-α(1,3)-Gal glycan.

40. The method of claim 39, wherein the colorectal cancer is advanced colorectal cancer.

41. The method of claim 39, wherein the antibody is administered via infusion to the subject at an initial dose of 400 mg/m$^2$ followed by a weekly dose of 250 mg/m$^2$.

42. The method of claim 39 wherein the antibody is produced in a Chinese Hamster Ovary (CHO) cell.

* * * * *

UNITED STATES PATENT AND TRADEMARK OFFICE
CERTIFICATE OF CORRECTION

PATENT NO.        : 10,118,966 B2
APPLICATION NO.   : 15/541291
DATED             : November 6, 2018
INVENTOR(S)       : Weizhu Qian It is certified that error appears in the above-identified patent and that said Letters Patent is hereby corrected as shown below:

In the Specification

Column 17, Line 9, "Mill" should be --MRI--.

In the Claims

Column 34, Line 9, Claim 17, "~36° C., preferably 34° C." should be --~36° C.--.

Signed and Sealed this
Twenty-ninth Day of January, 2019

Andrei Iancu
*Director of the United States Patent and Trademark Office*

SEQUENCE LISTING

```
<160> NUMBER OF SEQ ID NOS: 14

<210> SEQ ID NO 1
<211> LENGTH: 642
<212> TYPE: DNA
<213> ORGANISM: Artificial sequence
<220> FEATURE:
<223> OTHER INFORMATION: synthetic
<220> FEATURE:
<221> NAME/KEY: misc_feature
<223> OTHER INFORMATION: sequence encoding cetuximab light chain
```

<400> SEQUENCE: 1

```
gatatccttc tgacacagtc tccagtgata ctgtcagttt ctccagggga gcgcgtctca    60
tttagttgtc gggccagtca gagtatcggc acaaacatcc attggtacca gcagcggaca   120
aacggctccc cccggttgct cattaagtac gcaagcgagt ctatctctgg gataccaagt   180
cgcttctcgg gtagtggtag cggaacagat tttactctga gtatcaatag cgtcgaatcc   240
gaagatattg ccgattacta ctgtcagcag aataacaact ggccaaccac attcggcgcc   300
ggtaccaagc tggaactcaa gcgcacagtt gccgcaccta gtgtcttcat cttcccacca   360
tctgacgagc aactaaagag tggcactgca agtgtcgtat gtctgctgaa caacttttac   420
ccacgggagg ctaaagtgca gtggaaggta gacaacgccc ttcagagcgg aaattctcag   480
gaaagcgtca ccgaacaaga ttccaaggat agcacatact ccctgtcctc taccctgaca   540
ctgtcaaaag ctgactacga aaagcataaa gtgtatgctt gcgaggtgac tcatcagggg   600
ctcagctcgc ccgtcaccaa gtccttcaac cgtggagaat gt                      642
```

<210> SEQ ID NO 2
<211> LENGTH: 214
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: cetuximab light chain

<400> SEQUENCE: 2

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 1347
<212> TYPE: DNA
<213> ORGANISM: Artificial sequence
<220> FEATURE:
<223> OTHER INFORMATION: synthetic
<220> FEATURE:
<221> NAME/KEY: misc_feature
<223> OTHER INFORMATION: sequence encoding cetuximab heavy chain

<400> SEQUENCE: 3

| | | | | | |
|---|---|---|---|---|---|
| caggtgcagc | tgaagcagag | cggaccaggc | ctggtccagc | cctcacagtc | cctgagcatt | 60 |
| acttgtactg | tgagtgggtt | ctcgttgacg | aactacgggg | tgcattgggt | gcgccagagt | 120 |
| cccggtaaag | gctggagtg | gttaggcgtg | atttggagcg | gcggtaacac | tgactataat | 180 |
| acccctttca | ccagtcgctt | gagtatcaat | aaggataatt | caaagtctca | agtgttttt | 240 |
| aagatgaact | ccctacagag | caacgatacg | gctatctact | actgtgcccg | cgcccttaca | 300 |
| tactacgact | atgagttcgc | ttattggggc | aggggaccct | tggtcactgt | gtctgcagct | 360 |
| tctacaaaag | ggccatccgt | gttcccactg | gcccccagtt | ccaagagcac | tagtggtggc | 420 |
| acagcagccc | tcgggtgcct | cgtgaaggat | tacttcccgg | agccagtgac | cgtcagttgg | 480 |
| aactccggcg | ctctaacaag | cggagtacat | acttttccag | ccgtgctgca | gtcttcaggg | 540 |
| ctttacagtc | tttcctccgt | tgtgacagtg | cccagcagca | gctgggcac | ccagacttat | 600 |
| atttgtaatg | tgaaccataa | gccttctaat | actaaggtgg | acaagagagt | tgagccaaag | 660 |
| tcctgtgaca | aaactcacac | atgccccct | tgcccagctc | ctgagttgtt | gggcggccct | 720 |
| tccgtcttcc | tgtttccccc | gaaacctaag | gatacccctga | tgatatctcg | gacaccagaa | 780 |
| gtgacatgcg | tcgtggtcga | tgtgtcacac | gaagaccctg | aggtgaaatt | taactggtac | 840 |
| gtagacggtg | tagaagttca | caacgctaag | acaaagcctc | gggaagagca | gtacaactca | 900 |
| acctaccgag | tagtgtccgt | gcttactgtt | ctgcaccagg | actggctgaa | tggaaaggaa | 960 |
| tataagtgta | agtgtccaa | taaggcactg | cctgctccaa | tcgagaagac | gatttctaaa | 1020 |
| gccaagggac | aaccaagaga | acctcaggtg | tataccttgc | ccccatctag | agaagagatg | 1080 |
| accaaaaacc | aggtgtcact | tacatgcctc | gtgaaaggct | tctatccttc | tgacattgcc | 1140 |
| gtcgaatggg | agagtaacgg | acagcccgag | aacaactaca | agaccacacc | tccagtgctg | 1200 |
| gattcggatg | gctctttctt | cctttatagt | aagctcactg | tggacaagtc | ccgatggcag | 1260 |
| caggggaacg | tgttctcttg | cagcgtgatg | cacgaggcat | tgcataatca | ctacacccag | 1320 |
| aagtctctct | cattatcccc | tggcaag | | | | 1347 |

<210> SEQ ID NO 4
<211> LENGTH: 449
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: cetuximab heavy chain

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

-continued

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
         50                  55                  60

Ser Arg Leu Ser Ile Asn Lys Asp Asn Ser Lys Ser Gln Val Phe Phe
65                   70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
             100                 105                 110

Thr Leu Val Thr Val Ser Ala Ala Ser Thr Lys Gly Pro Ser Val Phe
             115                 120                 125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Arg Val Glu Pro Lys Ser Cys Asp Lys
         210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
         290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
         355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
         435                 440                 445

Lys

```
<210> SEQ ID NO 5
<211> LENGTH: 108
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: variable region of light chain

<400> SEQUENCE: 5

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 6
<211> LENGTH: 11
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: CDR1 of light chain

<400> SEQUENCE: 6

Arg Ala Ser Gln Ser Ile Gly Thr Asn Ile His
1               5                   10

<210> SEQ ID NO 7
<211> LENGTH: 7
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: CDR2 of light chain

<400> SEQUENCE: 7

Tyr Ala Ser Glu Ser Ile Ser
1               5

<210> SEQ ID NO 8
<211> LENGTH: 9
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: CDR3 of light chain

<400> SEQUENCE: 8
```

```
Gln Gln Asn Asn Asn Trp Pro Thr Thr
1               5
```

<210> SEQ ID NO 9
<211> LENGTH: 119
<212> TYPE: PRT
<213> ORGANISM: Artificial sequence
<220> FEATURE:
<223> OTHER INFORMATION: syntehtic
<220> FEATURE:
<221> NAME/KEY: MISC_FEATURE
<223> OTHER INFORMATION: variable region of light chain

<400> SEQUENCE: 9

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115
```

<210> SEQ ID NO 10
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: CDR1 of heavy chain

<400> SEQUENCE: 10

```
Asn Tyr Gly Val His
1               5
```

<210> SEQ ID NO 11
<211> LENGTH: 16
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: CDR2 of heavy chain

<400> SEQUENCE: 11

```
Val Ile Trp Ser Gly Gly Asn Thr Asp Tyr Asn Thr Pro Phe Thr Ser
1               5                   10                  15
```

<210> SEQ ID NO 12
<211> LENGTH: 11
<212> TYPE: PRT
<213> ORGANISM: Artificial sequence
<220> FEATURE:

```
<223> OTHER INFORMATION: synthetic
<220> FEATURE:
<221> NAME/KEY: MISC_FEATURE
<223> OTHER INFORMATION: CDR3 of heavy chain

<400> SEQUENCE: 12

Ala Leu Thr Tyr Tyr Asp Tyr Glu Phe Ala Tyr
1               5                   10

<210> SEQ ID NO 13
<211> LENGTH: 25
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<223> OTHER INFORMATION: Signal peptide

<400> SEQUENCE: 13

Met Ala Thr Met Val Pro Ser Ser Val Pro Cys His Trp Leu Leu Phe
1               5                   10                  15

Leu Leu Leu Leu Phe Ser Gly Ser Ser
            20                  25

<210> SEQ ID NO 14
<211> LENGTH: 75
<212> TYPE: DNA
<213> ORGANISM: Artificial sequence
<220> FEATURE:
<223> OTHER INFORMATION: synthetic
<220> FEATURE:
<221> NAME/KEY: misc_feature
<223> OTHER INFORMATION: sequence encoding signal peptide

<400> SEQUENCE: 14
atggccacca tggtgccctc ttctgtgccc tgccactggc tgctgttcct gctgctgctg      60
ttctctggct cttct                                                      75
```